United States Patent
Safai et al.

(10) Patent No.: US 9,217,713 B1
(45) Date of Patent: Dec. 22, 2015

(54) SYSTEM AND METHOD FOR DETECTING PIN-HOLES IN FIBERGLASS AND COMPOSITE PARTS

(71) Applicant: The Boeing Company, Chicago, IL (US)

(72) Inventors: Morteza Safai, Newcastle, WA (US); Ronald G. Turner, Arlington, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 14/309,713

(22) Filed: Jun. 19, 2014

(51) Int. Cl.
| | |
|---|---|
| *G01N 21/00* | (2006.01) |
| *G01N 21/88* | (2006.01) |
| *G01N 21/21* | (2006.01) |
| *G01N 21/84* | (2006.01) |

(52) U.S. Cl.
CPC ............ *G01N 21/8851* (2013.01); *G01N 21/21* (2013.01); *G01N 21/8806* (2013.01); *G01N 2021/845* (2013.01); *G01N 2021/888* (2013.01); *G01N 2021/8848* (2013.01); *G01N 2021/8861* (2013.01)

(58) Field of Classification Search
CPC ............ G01N 2021/4707; G01N 2021/4711; G01N 2021/4792; G01N 2021/556; G01N 2021/8848; G01N 2021/8864; G01N 2021/8877; G01N 2021/8896; G01N 21/21; G01N 21/47; G01N 21/4738; G01N 21/474; G01N 21/55
See application file for complete search history.

(56) References Cited

U.S. PATENT DOCUMENTS

| | | | |
|---|---|---|---|
| 5,424,536 A | 6/1995 | Moriya | |
| 6,320,654 B1 * | 11/2001 | Alders et al. | 356/237.2 |
| 8,588,262 B1 | 11/2013 | Safai | |
| 8,692,201 B1 | 4/2014 | Gordon, III et al. | |
| 2002/0141632 A1 * | 10/2002 | Engelbart et al. | 382/141 |
| 2005/0025350 A1 * | 2/2005 | Engelbart et al. | 382/141 |
| 2005/0117793 A1 * | 6/2005 | Engelbart et al. | 382/141 |
| 2005/0203657 A1 * | 9/2005 | Engelbart et al. | 700/110 |
| 2006/0181700 A1 * | 8/2006 | Andrews et al. | 356/237.2 |
| 2008/0055591 A1 | 3/2008 | Walton | |
| 2009/0207244 A1 | 8/2009 | Redko et al. | |
| 2013/0155400 A1 | 6/2013 | Nakao et al. | |

OTHER PUBLICATIONS

European Patent Office Extended Search Report for Application No. EP 15172787 dated Oct. 15, 2015.

* cited by examiner

*Primary Examiner* — Michael P Stafira
(74) *Attorney, Agent, or Firm* — John S. Economou

(57) ABSTRACT

A system and method is disclosed for detecting defects in the surface of a workpiece such as a fiberglass or composite part. A light source is positioned to direct light at the workpiece at an oblique angle with respect to the surface of the workpiece. At least one camera is positioned to detect light reflected from the workpiece and to generate a light signal corresponding to the reflected light. A polarizing lens is positioned between each of the at least one cameras and the workpiece. A processor is coupled to each of the at least one cameras to receive the corresponding light signals. The processor is programmed to process the light signals to detect any defects in the surface of the workpiece based on relative magnitudes of the received light signal. A video display and a printer are preferably coupled to the processor to show any detected defects.

20 Claims, 3 Drawing Sheets

SYSTEM AND METHOD FOR DETECTING PIN-HOLES IN FIBERGLASS AND COMPOSITE PARTS

FIELD

This disclosure relates generally to a system and method for detecting pin-holes and other surface deformities in fiberglass and composite parts.

BACKGROUND

Fiberglass and composite parts may develop pinhole surface defects during manufacturing. Such pinhole defects are typically generated after a part has gone through a high temperature curing, e.g., in an autoclave. Pinhole defects can be as small as 0.001 inch in diameter and are thus extremely difficult to detect with the naked eye. There are no currently known nondestructive testing techniques available for detection of pinholes on bare (unpainted) fiberglass and composite parts. After a part has been painted with pinholes on the surface, the pinhole defects become easier to detect and a painted part having pinhole defects will likely be rejected by the customer. However, repairing a part with pinhole defects after painting can be very expensive and time consuming. Many fiberglass and composite parts are formed over internal honeycomb structures, and pinhole defects can provide a much higher surface porosity than desired through the fiberglass or composite layer.

To overcome problems with fiberglass and composite parts having pinhole defects, it is common to coat all manufactured fiberglass and composite parts with a filter-type material. Parts coated in this manner must also be sanded after the filler-type material dries and before painting. The additional steps of coating and sanding every part, whether or not a pinhole exists in such part, is costly, time-consuming and generates a great deal of chemical waste.

Accordingly, there is a need for a system and method which overcomes the drawbacks of the conventional systems and methods described above.

SUMMARY

In one aspect, a system for detecting defects in a surface of a workpiece which includes a light source, at least one light detector, a polarizing lens for each light detector and a processor. The light source is positioned to direct light at the workpiece at an oblique angle with respect to the surface of the workpiece. The at least one light detector is positioned to detect light reflected from the workpiece and to generate a light signal corresponding to the reflected light. The polarizing lenses are respectively positioned between each of the at least one light detectors and the workpiece. The a processor coupled to each of the at least one light detectors to receive the corresponding light signals, the processor programmed to process the light signals to detect any defects in the surface of the workpiece based on relative magnitudes of the received light signal.

In one further embodiment, a display device may be coupled to the processor, with the processor also programmed to provide a video signal to the display device which shows, on the display device, the workpiece and any detected defects on the workpiece.

In another further embodiment, a printer may be coupled to the processor, with the processor also programmed to provide a print signal to the printer to provide a printout which shows the workpiece and any detected defects on the workpiece.

In yet another further embodiment, a printer may be coupled to the processor and positioned to print directly on the workpiece, with the processor also programmed to provide a print signal to the printer to print a position of any detected defects directly on the workpiece.

Preferably, the at least one light detector consists of two light detectors. Each light detector may further be a camera. Each camera may preferably be a light-field camera. In addition, the light source may be a directional linear light source.

In another aspect, system for detecting defects in a surface of a workpiece includes a scanning head and a processor. The scanning head may be positioned above a conveyor belt and includes a light source, at least one light detector and a polarizing lens for each light detector. The light source is positioned to direct light at the workpiece at an oblique angle with respect to the surface of the workpiece. The at least one light detector is positioned to detect light reflected from the workpiece and to generate a light signal corresponding to the reflected light. The polarizing lenses are respectively positioned between each of the at least one light detectors and the workpiece. The processor is coupled to each of the at least one light detectors to receive the corresponding light signals. The processor is programmed to process the light signals to detect any defects in the surface of the workpiece based on relative magnitudes of the received light signal. The conveyor belt is for positioning the workpiece under the scanning head.

In one further embodiment, a display device may be coupled to the processor, with the processor also programmed to provide a video signal to the display device which shows, on the display device, the workpiece and any detected defects on the workpiece.

In another further embodiment, a printer may be coupled to the processor, with the processor also programmed to provide a print signal to the printer to provide a printout which shows the workpiece and any detected defects on the workpiece.

In yet another further embodiment, a printer may be coupled to the processor and positioned to print directly on the workpiece after the workpiece passes under the scanning head on the conveyor belt, with the processor also programmed to provide a print signal to the printer to print a position of any detected defects directly on the workpiece.

Preferably, the at least one light detector consists of two light detectors. Each light detector may further be a camera. Each camera may preferably be a light-field camera. In addition, the light source may be a directional linear light source.

In yet another aspect, a method of detecting defects on a workpiece. Light is directed at the workpiece at an oblique angle with respect to the surface of the workpiece. Light reflected from the workpiece through a polarizing lens is detected in at least one light detector. A light signal corresponding to the detected reflected light is generated in each of the at least one light detectors. Finally, the light signals from each of the at least one light detectors is processed in the processor to detect any defects in the surface of the workpiece based on relative magnitudes of the received light signal. In a further embodiment, a video display is provided on a display device coupled to the processor that shows a position of each detected defect in the workpiece. In another further embodiment, a printout is provided on a printer coupled to the processor which shows a position of each detected defect in the workpiece. In yet another further embodiment, a position of each detected defect in the workpiece is printed directly on the workpiece, via a printer coupled to the processor.

The features, functions, and advantages that have been discussed can be achieved independently in various embodiments or may be combined in yet other embodiments, further details of which can be seen with reference to the following description and drawings.

BRIEF DESCRIPTION OF THE DRAWINGS

The following detailed description, given by way of example and not intended to limit the present disclosure solely thereto, will best be understood in conjunction with the accompanying drawings in which.

DETAILED DESCRIPTION

In the present disclosure, like reference numbers refer to like elements throughout the drawings, which illustrate various exemplary embodiments of the present disclosure.

Figure 1:
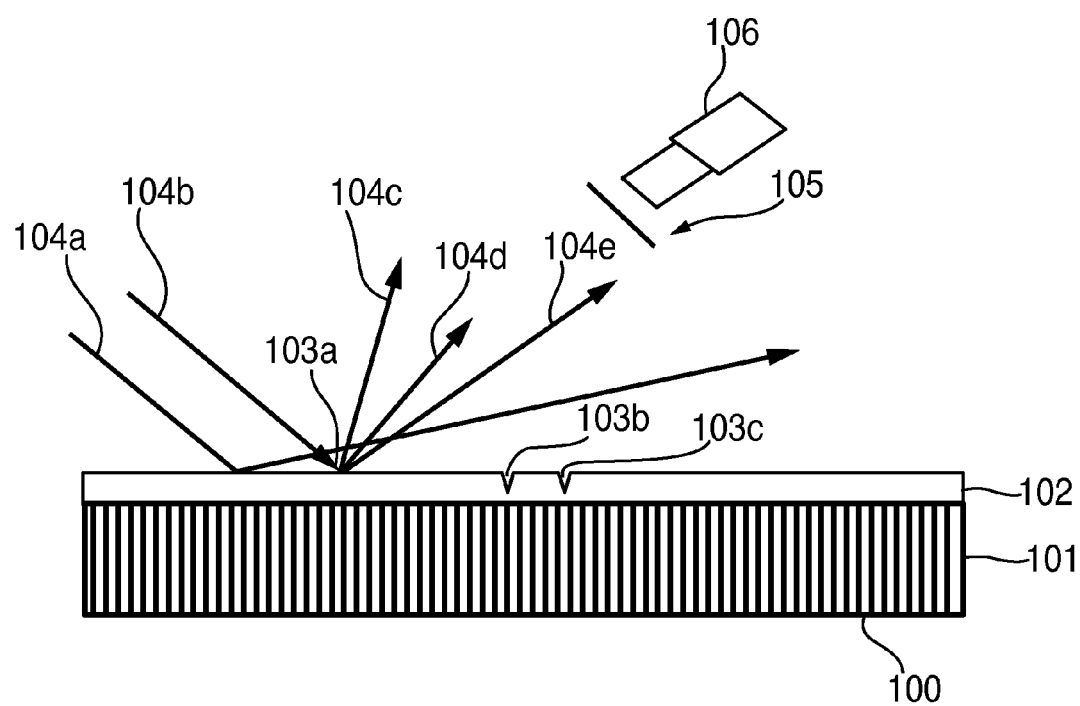
FIG. 1 is a block diagram showing how light is reflected by the surface of a part under test according to an aspect of the present disclosure.

Referring now to FIG. 1, a part 100 under test may consist of a shell portion 102 and an inner core portion 101. Part 100 may be an exterior panel, for example. The core portion 101 may provide structural support while the shell portion 102, which is the outer layer, may provide protection to the core portion from external environmental influences (e.g., moisture). The shell portion 102 may be formed from fiberglass or a composite material which, as discussed above, may develop pinhole or other surface defects during high temperature curing. In FIG. 1, three pinholes 103 are shown in shell portion 102 (but not to scale). As evident, pinholes 103a, 103b, 103c can weaken the structural integrity (at least with respect to porosity) even though such pinholes can be quite small (as small as 0.001 inch in diameter). As a result, the present disclosure provides a non-contact system and method for detecting and marking pinholes 103a, 103b, 103c so that only tested parts 100 which actually have pinholes or other surface defects need be repaired. By eliminating the conventional coating step and the necessary follow-up sanding step for every part, a significant cost-savings can be achieved. In addition, a significant reduction or even elimination of the waste products generated by the sanding step can also be achieved which greatly reduces the use of hazardous chemicals and the consequent environmental footprint of the part manufacturing process.

The system disclosed herein employs an imaging technique to identify pinholes in a fiberglass or composite part (generically a workpiece herein). The system includes a light source (not shown in FIG. 1) which directs light (shown by beams 104a, 104b) at a fixed oblique angle to part 100. A camera 106 is positioned to receive the reflected light beams through a polarization filter 105. Although a single camera 106 is shown in FIG. 1 for illustrative purposes, as discussed below, two cameras are preferably used to obtain stereo imaging of part 100 for accurate detection of small pinholes. The system directs a high intensity directional light at part 100 under test and monitors the light reflected off of part 100 with camera 106 and associated polarization filter 105. Preferably, the camera or cameras 106 are light field cameras to obtain a greater depth of field and obtain more accurate results. As shown in FIG. 1, when a diffused light with uniform intensity is eliminated on a part surface at certain angle (i.e., the light beam 104a), the scattering of light is proportional to the surface roughness (e.g., light beam 104b becomes beams 104c, 104d, 104e). Thus, when there is a pinhole 103a on the surface of shell portion 102, light will scatter differently from pinhole 103a than from the smooth surface of shell portion 102 and thus create a light flux variation on the detector of each camera 106. Because the pinholes in a part under test are usually quite small, the depth of field detection capability of cameras 106 is extremely important and thus a light-field (plenoptic) camera is preferable, although in some circumstances ordinary cameras may be employed and still obtain acceptable results. In addition, a polarizer filter 105 is preferably used in front of the lens of each camera 106 to eliminate light scattering detection from surroundings. Polarizing filter 105 eliminates unwanted reflection and glare from the surface of part 100. Polarizing filter 105 may be a linear polarizer or a circular polarizer or a combination of linear and circular polarizers.

As explained above, the system disclosed herein directs a beam of light onto a surface of a part under test and then detects the presence or absence of pinholes in the part based on the type of light that is reflected off the surface of such part. The reflected light is collected by at least one camera positioned at an angle sufficient to collect incident light scattering off pinholes located in the surface of the part. In particular, the at least one camera is positioned at an angle that at least matches, but is not less than, the angle of refraction of the light directed at the surface of the part under test. Light collected by the camera that is not due to pinholes such as glare or unwanted reflection from surroundings is filtered out via the polarization filter. As a result, this technique prevents the camera imagery sensor from being saturated with unwanted light rays which are not from the part surface and reduces the interference of unwanted light with the scatter light from a pinhole. This technique reduces the probability of failed pinhole detection and enhances the detection probability of pinholes with the camera.

Figure 2:
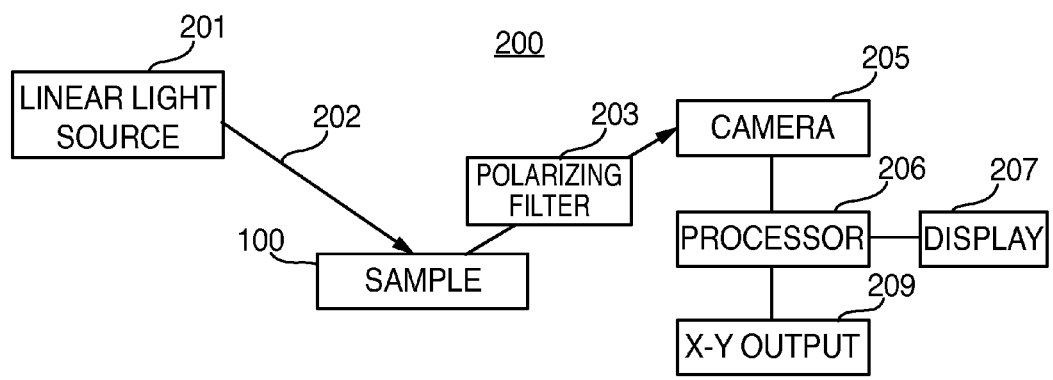
FIG. 2 is a block diagram of a first embodiment of a surface defect detection system according to the present disclosure.

Referring now to FIG. 2, a complete system 200 for testing a part 100 is shown. In particular, as shown in FIG. 2, a light source 201 directs a beam of light 202 at part 100 at an obtuse angle. Preferably, the light source 201 is a directional linear light source. The reflected light 203 is captured by a camera 205, preferably after passing through a polarizing filter 204. As discussed herein, preferably two cameras 205 are provided to obtain a stereo image of the surface of sample 100 and to obtain a more precise view of any pinholes in the surface of part 100. Cameras 205 are preferably light-field cameras. The signals from cameras 205 are provided to a processor 206, which is programmed to detect the presence of pinholes (or other surface defects) in part 100 based on the variation of light detected in the images of part 100 from the two cameras 205. Processor 206 is also programmed to provide a signal to display 207 indicating whether or not any pinholes have been detected in the current part 100 under test, and preferably to provide a video image of the part 100 under test showing the positions of each detected pinhole. In addition, an output device 207 is coupled to processor 206. Output device 207 may be a printer, e.g., a two axis (X—Y type) printer, which provides a printout of the current part 100 under test that can be used to identify and then repair each detected pinhole in the current part 100 under test. In an alternative embodiment, output device is a printer, e.g., a two-axis type printer, which is adapted to print directly on part 100, marking the area around each detected pinhole.

Figure 3:
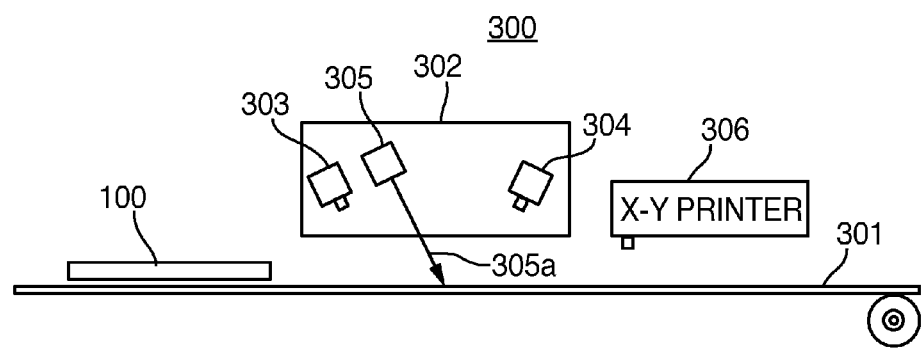
FIG. 3 is a block diagram of a second embodiment of a surface defect detection system according to the present disclosure.

Referring now to FIG. 3, an adaptation of the system of the present disclosure is shown for use with an automated test system 300. In particular, system 300 includes a conveyor belt 301 which moves the part 100 under test along under a scanning head 302. Scanning head 302 includes a light source 305 which generates a light beam 305a. Scanning head also includes two cameras 303, 304 for obtaining a stereo view of part 100 as it moves under scanning head 302 and as it is illuminated by light source 305. Preferably each camera 303, 304 includes a polarizing filter (not shown) for filtering the received light. System 300 includes a processor (not shown) which receives signals from each camera 303, 304 and detects the presence of pinholes or other surface defects in each part 100. A printer 306 may be provided coupled to the processor which receives signals from the processor identifying the location of any identified defects. For example, by synchronizing the movement of the part 100 under test along conveyor 301, printer 306 may be a one-axis printer that is able to mark pinholes as part 100 moves along the conveyor 301. Alternatively, printer 306 may be a two axis (i.e., X-Y) printer and the conveyor may move each part 100 in discrete steps along conveyor 301. With either type of printer, automated processing may be provided to identify and mark each detected pinhole in each part 100 as (or immediately after) it is tested. As one of ordinary skill in the art will readily recognize, printer 306 may be omitted in another alternative embodiment and a user may identify the pinhole defects using a separate display only.

Figure 4:
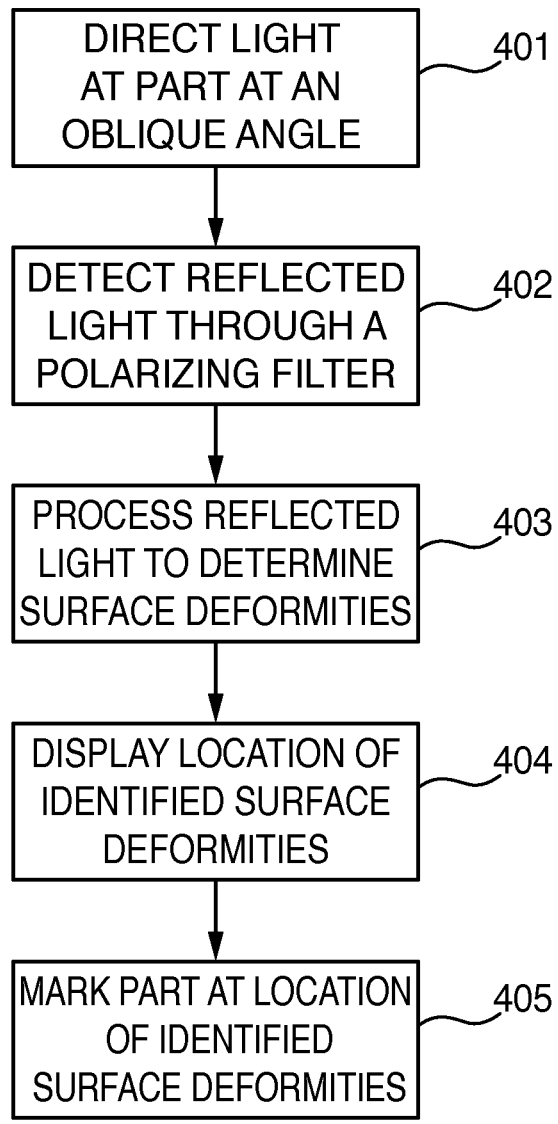
FIG. 4 is a flow chart of the operation of the embodiments of the systems according to the present disclosure.

Referring now to FIG. 4, the method of the present disclosure operates by first directing light at an oblique angle at a part under test (step 401). Next, the reflected light is detected by at least one (and preferably two) cameras, preferably light-field cameras, and preferably after passing through a polarizing filter (step 402). The images detected by each camera are processed to identify any pinholes present in the surface of the part under test (step 403), and the location of each detected pinhole is presented on a display (step 404). In further embodiment, the system automatically marks the surface of the part 100 under test (step 405). Step 405 may be provide in addition to step 404 or in the alternative to such step.

The identification and/or marking of any detected pinhole in a part under test allows such detected pinholes to be individually patched, as contrasted with conventional processing which coats and then sands every part, whether or not pinholes are present. By individually patching each detected pinhole, a dramatic decrease in the total amount of chemicals used for processing can be achieved over the conventional processing methods which blindly coated every part with filler chemicals whether or not pinholes are present. Furthermore, since the system disclosed herein should identify all pinholes, implementation of this system should also dramatically decrease (or even eliminate) returns/rework requested by customers.

Although the present disclosure has been particularly shown and described with reference to the preferred embodiments and various aspects thereof, it will be appreciated by those of ordinary skill in the art that various changes and modifications may be made without departing from the spirit and scope of the disclosure. It is intended that the appended claims be interpreted as including the embodiments described herein, the alternatives mentioned above, and all equivalents thereto.

What is claimed is:

1. A system for detecting defects in a surface of a workpiece, comprising:
   a light source positioned to direct light at the workpiece at a predetermined oblique angle with respect to the surface of the workpiece;
   at least one light detector positioned at the predetermined oblique angle with respect to the surface of the workpiece to detect light reflected from the workpiece and to generate a light signal corresponding to the reflected light;
   a polarizing lens positioned between each of the at least one light detectors and the workpiece; and
   a processor coupled to each of the at least one light detectors to receive the corresponding light signals, the processor programmed to process the light signals to detect any defects in the surface of the workpiece based on relative magnitudes of the received light signals;
   wherein the at least one light detector comprises two light detectors;
   wherein each light detector comprises a camera; and
   wherein each camera comprises a light-field camera.

2. The system of claim 1, further comprising a display device coupled to the processor, and wherein the processor is also programmed to provide a video signal to the display device which shows, on the display device, the workpiece and any detected defects on the workpiece.

3. The system of claim 1, further comprising a printer coupled to the processor, and wherein the processor is also programmed to provide a print signal to the printer to provide a printout which shows the workpiece and any detected defects on the workpiece.

4. The system of claim 1, further comprising a printer coupled to the processor and positioned to print directly on the workpiece, and wherein the processor is also programmed to provide a print signal to the printer to print a position of any detected defects directly on the workpiece.

5. The system of claim 1, wherein the light source is a directional linear light source.

6. A system for detecting defects in a surface of a workpiece, comprising:
   a scanning head positioned above a conveyor belt and comprising:
      a light source positioned to direct light at the workpiece at a predetermined oblique angle with respect to the surface of the workpiece;
      at least one light detector positioned at the predetermined oblique angle with respect to the surface of the workpiece to detect light reflected from the workpiece and to generate a light signal corresponding to the reflected light;
      a polarizing lens positioned between each of the at least one light detectors and the workpiece; and
      a processor coupled to each of the at least one light detectors to receive the corresponding light signals, the processor programmed to process the light signals to detect any defects in the surface of the workpiece based on relative magnitudes of the received light signals, and
   wherein the conveyor belt is for positioning the workpiece under the scanning head;
   wherein the at least one light detector comprises two light detectors;
   wherein each light detector comprises a camera;
   wherein each camera comprises a light-field camera.

7. The system of claim 6, further comprising a display device coupled to the processor, and wherein the processor is also programmed to provide a video signal to the display device which shows, on the display device, the workpiece and any detected defects on the workpiece.

8. The system of claim 7, further comprising a printer coupled to the processor, and wherein the processor is also programmed to provide a print signal to the printer to provide a printout which shows the workpiece and any detected defects on the workpiece.

9. The system of claim 7, further comprising a printer coupled to the processor and positioned to print directly on the workpiece after the workpiece passes under the scanning head on the conveyor belt, and wherein the processor is also programmed to provide a print signal to the printer to print a position of any detected defects directly on the workpiece.

10. The system of claim 7, wherein the light source is a directional linear light source.

11. A method of detecting defects in a surface of a workpiece, comprising the steps of:
   directing light at the workpiece at a predetermined oblique angle with respect to the surface of the workpiece;
   detecting, in at least one light-field camera positioned at the predetermined oblique angle with respect to the surface of the workpiece, light reflected from the workpiece through a polarizing lens;
   generating, in each of the at least one light-field cameras, a light signal corresponding to the detected reflected light;
   processing, in a processor, the light signals from each of the at least one light-field cameras to detect any defects in the surface of the workpiece based on relative magnitudes of the light signals from each of the at least one light detectors.

12. The method of claim 11, further comprising the step of providing a video display, on a display device coupled to the processor, showing a position of each detected defect in the workpiece.

13. The method of claim 11, further comprising the step of providing a printout, on a printer coupled to the processor, showing a position of each detected defect in the workpiece.

14. The method of claim 11, further comprising the step of printing directly on the workpiece, via a printer coupled to the processor, a position of each detected defect in the workpiece.

15. The method of claim 11, wherein the step of directing light at the workpiece is performed using a directional linear light source.

16. The system of claim 1, wherein the processor is programmed to generate a stereo image of the surface of the workpiece based on each received light signal while processing the light signals to detect any defects in the surface of the workpiece.

17. The system of claim 6, wherein the processor is programmed to generate a stereo image of the surface of the workpiece based on each received light signal while processing the light signals to detect any defects in the surface of the workpiece.

18. The method of claim 11, wherein the step of processing the light signals includes generating stereo image of the surface of the workpiece based on each received light signal.

19. The system of claim 1, further comprising a display device coupled to the processor, and wherein the processor is also programmed to provide a signal to the display device which indicates that a defect has been detected on the workpiece.

20. The system of claim 6, further comprising a display device coupled to the processor, and wherein the processor is also programmed to provide a signal to the display device which indicates that a defect has been detected on the workpiece.

* * * * *